United States Patent [19]

Lincoln

[11] 4,354,021

[45] Oct. 12, 1982

[54] 2-DECARBOXY-2-TETRAZOLYL-6-ALKOXY-PGI₁ COMPOUNDS

[75] Inventor: Frank H. Lincoln, Portage, Mich.

[73] Assignee: The Upjohn Company, Kalamazoo, Mich.

[21] Appl. No.: 70,952

[22] Filed: Aug. 30, 1979

Related U.S. Application Data

[62] Division of Ser. No. 892,108, Mar. 31, 1978, Pat. No. 4,207,402.

[51] Int. Cl.³ .................. C07D 405/06; C07D 405/12
[52] U.S. Cl. .................................... 542/431; 548/252; 548/253
[58] Field of Search ................. 548/252; 542/426, 431

[56] References Cited

U.S. PATENT DOCUMENTS

| | | | |
|---|---|---|---|
| 4,125,713 | 11/1978 | Nelson | 548/252 |
| 4,130,569 | 12/1978 | Kelly | 548/252 |
| 4,225,507 | 9/1980 | Sin | 548/250 |
| 4,235,997 | 11/1980 | Lincoln | 200/346.22 |
| 4,236,000 | 11/1980 | Lincoln | 260/346.22 |

Primary Examiner—David B. Springer
Attorney, Agent, or Firm—L. Ruth Hattan; Robert A. Armitage

[57] ABSTRACT

Prostacyclin I₁, (PGI₁) derivatives and analogs having a 6-alkoxy feature and having pharmacological activity and processes for preparing them are disclosed.

1 Claim, No Drawings

2-DECARBOXY-2-TETRAZOLYL-6-ALKOXY-PGI$_1$ COMPOUNDS

DESCRIPTION

CROSS REFERENCE TO RELATED APPLICATIONS

This application is a divisional application of Ser. No. 892,108, filed Mar. 31, 1978, now U.S. Pat. No. 4,207,402.

BACKGROUND OF THE INVENTION

The present invention relates to novel 2-decarboxy-2-tetrazolyl-6-alkoxy-PGI$_1$ compounds, useful as pharmaceutical agents, principally for the induction of certain prostacyclin-like pharmacological effects. The essential material of consisting description of the preparation and use of these substances is incorporated here by reference from Ser. No. 892,108, filed Mar. 31, 1978, now U.S. Pat. No. 4,207,242.

SUMMARY OF THE INVENTION

The present invention particularly relates to a compound of formula 1

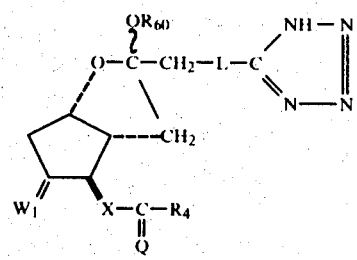

wherein L is
(1) —(CH$_2$)$_d$—C(R$_2$)$_2$—,
(2) —(CH$_2$—O—CH$_2$—Y—, or
(3) —(CH$_2$CH═CH—,
wherein d is zero to 5, R$_2$ is hydrogen, methyl or fluoro, being the same or different with the proviso that one R$_2$ is not methyl when the other is fluoro, and Y is a valence bond, —CH$_2$—, or —(CH$_2$)$_2$—;
wherein Q is oxo, α—H:β—H, α—R$_8$:β—OH, or α—OH:β—R$_8$, wherein R$_8$ is hydrogen or alkyl of one to 4 carbon atoms, inclusive;
wherein R$_4$ is
(1) —C(R$_5$)(R$_6$)—C$_g$H$_{2g}$—CH$_3$,
(2) —C(R$_5$)(R$_6$)—Z—(Ph), or
(3) cis—CH$_2$—CH═CH—CH$_2$CH$_3$,
wherein C$_g$H$_{2g}$ is alkylene of one to 9 carbon atoms, inclusive, with one to 5 carbon atoms, inclusive, in the chain between —CR$_5$R$_6$— and terminal methyl, wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro and the further proviso that neither R$_5$ nor R$_6$ is fluoro when Z is oxa (—O—); wherein Z represents an oxa atom (—O—) or C$_j$H$_{2j}$ wherein C$_j$H$_{2j}$ is a valence bond or alkylene of one to 9 carbon atoms, inclusive, with one to 6 carbon atoms, inclusive between CR$_5$R$_6$— and the (Ph);
wherein (Ph) is phenyl or phenyl substituent by (T)s, wherein T is alkyl of one to 4 carbon atoms, inclusive, fluoro, chloro, trifluoromethyl, or —OR$_7$, wherein R$_7$ is alkyl of one to 4 carbon atoms, inclusive; and wherein s is zero, one, 2 or 3, with the proviso that not more than two T's are other than alkyl and when s is 2 or 3 the T's are either the same or different;
wherein W$_1$ is α—OH:β—H, α—H:β—OH, oxo, methylene, α—H:β—H, or α—CH$_2$OH:β—H;
wherein R$_{60}$ is straight-chain alkyl of one to 6 carbon atoms, inclusive; and
wherein X is
(1) trans—CH═CH—,
(2) cis—CH═CH—,
(3) —C≡C—, or
(4) —CH$_2$CH$_2$—.

With regard to the divalent substituents described above, e.g., Q and W$_1$, these divalent radicals are defined as α—R$_i$:β—R$_j$, where R$_i$ represents a substituent of the divalent moiety of the alpha configuration with respect to the cyclopentane ring and R$_j$ represents a substituent of the divalent moiety of the beta configuration with respect to the cyclopentane ring. Accordingly, when Q is defined as α—OH:β—R$_8$, the hydroxy of the Q moiety is in the alpha configuration, i.e. as in prostacyclin, and the R$_8$ substituent is in the beta configuration. Not all carbon atoms to which such divalent moieties are attached represent asymmetric centers. For example, when both valence bonds are to hydrogen (e.g., W$_1$ or Q is α—H:β—H), then no asymmetric center is present.

I claim:
1. A compound of the formula

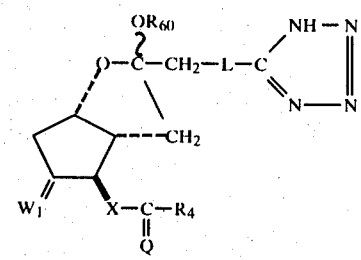

wherein L is
(1) —(CH$_2$)$_d$—C(R$_2$)$_2$—,
(2) —CH$_2$—O—CH$_2$—Y—, or
—CH$_2$CH═CH—,
wherein d is zero to 5, R$_2$ is hydrogen, methyl or fluoro, being the same or different with the proviso that one R$_2$ is not methyl when the other is fluoro, and Y is a valence bond, —CH$_2$—, or —(CH$_2$)$_2$—;
wherein
Q is oxo, α—H:β—H, α—R$_8$:β—OH, or α—OH:β—R$_8$, wherein R$_8$ is hydrogen or alkyl of one to 4 carbon atoms, inclusive;
wherein R$_4$ is
(1) —C(R$_5$)(R$_6$)—C$_g$H$_{2g}$—CH$_3$,
(2) —C(R$_5$)(R$_6$)—Z—(Ph), or
(3) cis—CH$_2$—CH═CH—CH$_2$CH$_3$,
wherein C$_g$H$_{2g}$ is alkylene of one to 9 carbon atoms, inclusive, with one to 5 carbon atoms, inclusive, in the chain between —CR$_5$R$_6$— and terminal methyl, wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro and the further proviso that neither R$_5$ nor R$_6$ is fluoro when Z is oxa (—O—); wherein Z represents an oxa atom (—O—) or C$_j$H$_{2j}$ wherein C$_j$H$_{2j}$ is a valence bond or alkylene of one to 9 carbon atoms, inclusive, with one to 6 carbon atoms, inclusive between $CR_5R_6-$ and the (Ph);

wherein (Ph) is phenyl or phenyl substituent by (T)s, wherein T is alkyl of one to 4 carbon atoms, inclusive, fluoro, chloro, trifluoromethyl, or $-OR_7$, wherein $R_7$ is alkyl of one to 4 carbon atoms, inclusive, and s is zero, one, 2 or 3, with the proviso that not more than two T's are other than alkyl and when s is 2 or 3 the T's are either the same or different;

wherein $W_1$ is $\alpha-OH:\beta-H$, $\alpha-H:\beta-OH$, oxo, methylene, $\alpha-H:\beta-H$, or $\alpha-CH_2OH:\beta-H$;

wherein $R_{60}$ is straight-chain alkyl of one to 6 carbon atoms, inclusive; and wherein X is
 (1) trans—CH=CH—,
 (2) cis—CH=CH—,
 (3) —C≡C—, or
 (4) —CH$_2$CH$_2$—.

* * * * *